(12) United States Patent
Brooker et al.

(10) Patent No.: US 12,618,036 B2
(45) Date of Patent: May 5, 2026

---

(54) TECHNIQUE AND PARTS KIT FOR SEALING AN INCUBATOR IN A WALL

(71) Applicant: Caron Products and Services, Inc., Marietta, OH (US)

(72) Inventors: Steven F. Brooker, Marietta, OH (US); Robert W. Dotterer, Sardis, OH (US)

(73) Assignee: CARON PRODUCTS AND SERVICES, INC., Marietta, OH (US)

( * ) Notice: Subject to any disclaimer, the term of this patent is extended or adjusted under 35 U.S.C. 154(b) by 814 days.

(21) Appl. No.: 17/866,504

(22) Filed: Jul. 16, 2022

(65) Prior Publication Data

US 2023/0019480 A1     Jan. 19, 2023

Related U.S. Application Data

(60) Provisional application No. 63/222,731, filed on Jul. 16, 2021.

(51) Int. Cl.
*C12M 1/00* (2006.01)
*C12M 1/12* (2006.01)

(52) U.S. Cl.
CPC ............ *C12M 23/50* (2013.01); *C12M 37/04* (2013.01)

(58) Field of Classification Search
CPC .............................. C12M 23/50; C12M 37/04
USPC ....................................................... 435/289.1
See application file for complete search history.

(56) References Cited

U.S. PATENT DOCUMENTS 9,389,013 B2 * 7/2016 Rolek ................... A47F 3/0426

FOREIGN PATENT DOCUMENTS

EP          2985551 A1 * 2/2016 ........... F25D 23/085
EP          2985551 B1 * 12/2017 ........... A47F 3/0426

* cited by examiner

*Primary Examiner* — Michael L Hobbs
*Assistant Examiner* — Lenora A Abel
(74) *Attorney, Agent, or Firm* — John L. DeAngelis; Wolter Van Dyke Davis, PLLC

(57) ABSTRACT

A kit of parts for sealing openings between an enclosure extending through a wall separating a cleanroom and a space outside the cleanroom. Multiple gaskets, frame members, and a lower skirt are positioned to seal any openings between the side, top and bottom surfaces of the enclosure and proximate wall surfaces. The sealing components can be easily installed without the use of tools.

19 Claims, 4 Drawing Sheets

TECHNIQUE AND PARTS KIT FOR SEALING AN INCUBATOR IN A WALL

CROSS REFERENCE TO RELATED APPLICATIONS

This application claims benefit of Provisional Application No. 63/222,731, filed Jul. 16, 2021, the entire contents of which are incorporated by reference as if fully set forth herein, under 35 U.S.C. § 119(e).

BACKGROUND OF THE INVENTION

Culturing cells is a common laboratory practice for many industrial markets. Optimal cell growth environments are created within an incubator where the temperature, humidity, and $CO_2$ (or oxygen) levels are controlled. Contamination is the biggest threat to cell culturing and extensive steps are taken to maintain clean incubator environments.

One technique for maintaining a clean environment locates the cell cultures in an incubator and then places the entire incubator in a cleanroom. But incubators in cleanrooms have certain known disadvantages:

Expensive to build cleanrooms

Expensive to maintain cleanrooms

Time consuming for personnel to enter and exit cleanrooms

Risk of contamination with each cleanroom entry/exit

Expense of maintaining clean linens for use in the cleanroom

Difficulty maintaining equipment in a cleanroom; many servicing procedures can't be performed in a cleanroom and therefore the equipment must be removed and serviced outside the cleanroom, then returned to the clean room.

To address these issues, one solution locates the front (i.e., door) of the incubator inside a cleanroom while the remainder of the incubator protrudes through a cleanroom wall into a space outside the cleanroom. To accomplish this, a hole the size of the incubator, is cut into the wall and the incubator is installed in that opening, with the front surface extending about 6 inches into the cleanroom. This arrangement advantageously maintains the culturing cells in a clean environment, while locating the incubator maintenance section outside the cleanroom. This arrangement also minimizes the cleanroom space occupied by the incubator.

Prior art FIG. 1 illustrates three incubator doors 10 visible and accessible from inside the cleanroom; the portion of the incubator extending into the cleanroom is referred to as the forward incubator portion. Although it is difficult to visualize from the angle of FIG. 1, the doors and proximate side surfaces protrude about 6 inches into the cleanroom.

FIG. 2 illustrates a rear portion 12 of an incubator extending into a space outside the cleanroom; the portion of the incubator extending into the space outside the cleanroom is referred to as the rearward incubator portion. Most of the incubator mechanical and electrical components are located in this rearward portion and thus can be easily accessed and maintained without entering the cleanroom.

As is known, incubators are typically designed to be placed entirely in one room and were not intended to be installed with a first portion inside and a second portion outside the cleanroom, as described above and illustrated in FIGS. 1 and 2.

The incubator exterior surfaces often have protrusions and are typically not perfectly flat. When installed in a cleanroom wall (such as illustrated in FIGS. 1 and 2) and without an effective seal, the incubator surfaces allow outside contaminants to enter the cleanroom.

Along the bottom surface of the incubator, casters, leveling feet, door hinges, tubing drains, etc. also present difficulties in creating and maintaining an effective seal, thereby jeopardizing a contaminant-free cleanroom atmosphere. The underside surface of an incubator is illustrated in FIG. 4, showing casters 14, leveling feet 16 and other protrusions that make forming an air tight seal along a cleanroom floor surface difficult.

The cleanroom (into which the incubator opens) must be isolated from the outside environment (where the incubator rearward portion is located). To maintain the cleanroom environment and ensure that chemicals and substances used to clean and otherwise maintain the cleanroom do not infiltrate outside the cleanroom, mechanical seals between the cleanroom wall and floor surfaces, and the incubator surfaces must be vapor tight. Also, when the incubator door is open, air must be prevented from flowing from the cleanroom/incubator front side, through the incubator chamber to the non-cleanroom/incubator rearward portion and then into the non-cleanroom space. While maintaining this internal incubator barrier is not addressed by the elements of the "kit of parts" of the present invention, it is a necessary incubator feature that is required to maintain the cleanroom atmosphere.

It should also be noted that the cleanroom is maintained at a positive pressure relative to the pressure outside the cleanroom. This pressure differential prevents contamination outside the cleanroom from entering the cleanroom.

BRIEF DESCRIPTION OF THE FIGURES

The present invention can be more easily understood and the advantages and uses thereof more readily apparent when the detailed description of the present invention is read in conjunction with the figures wherein.

In accordance with common practice, the various described and illustrated features are not drawn to scale, but are drawn to emphasize specific characteristics relevant to the invention. Like reference numerals denote like elements throughout the figures and text.

DETAILED DESCRIPTION OF THE INVENTION

The present invention resolves the disadvantages cited above and comprises a parts kit (a plurality of components) that allows an "incubator in a wall" to be installed quickly and easily, and additionally provides an effective barrier between the cleanroom and the space outside the cleanroom.

The parts kit comprises two key elements:

A frame for closing a gap between the side and top surfaces of the incubator and the proximate wall surfaces (sometimes referred to as opposing wall surface) through which the incubator passes. The frame and its associated parts:

Provides a double vapor barrier

Attaches/assembles to the incubator with no mechanical fasteners

Does not require the use of any caulking material or any technique-sensitive processes Adapts to manufacturing variations in the flatness of the incubator surfaces as well as any construction variations in the wall cutout Provides vibration dampening between the incubator and the wall Frame material is resistant to harsh cleanroom chemicals A bottom skirt that:

Comprises a three-sided wrap-around skirt (i.e., around the incubator front and side surfaces), enclosing the casters and feet that protrude from the bottom surface of the incubator Has coved corners (in the lower skirt region) for easy cleaning (unlike a corner or crack that can harbor contaminates and is difficult to clean). See FIG. 6.

Allows easy access to the incubator leveling screws that provide independent incubator leveling (i.e., from the floor) for adjusting both the height above the floor and for ensuring that the incubator bottom surface is level.

Fastener-less installation

Skirt material that is resistant to commonly-used harsh cleanroom chemicals

A top surface of the skirt is in a sealed relation with a bottom surface of the incubator.

A bottom surface of the skirt is proximate the floor surface on which the incubator sets and is also in a sealed relation with the floor surface.

Figure 1:
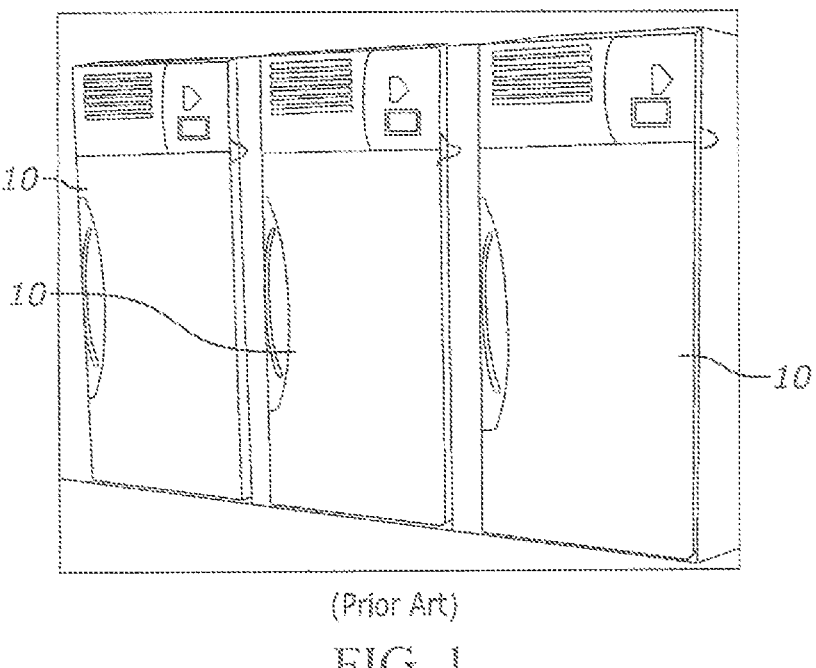
FIG. 1 is a prior art illustration of a forward portion of incubators mounted within a wall of a cleanroom.
Figure 2:
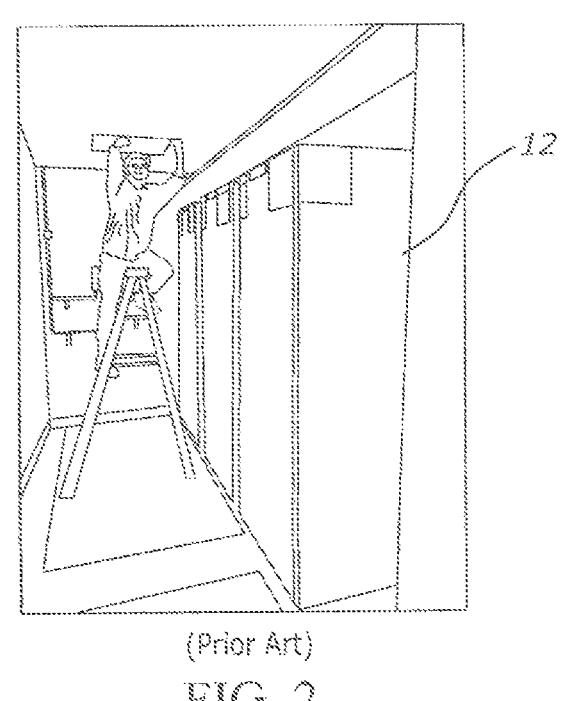
FIG. 2 is a prior art illustration a rearward portion of incubators mounted within a wall of a cleanroom.
Figure 3:
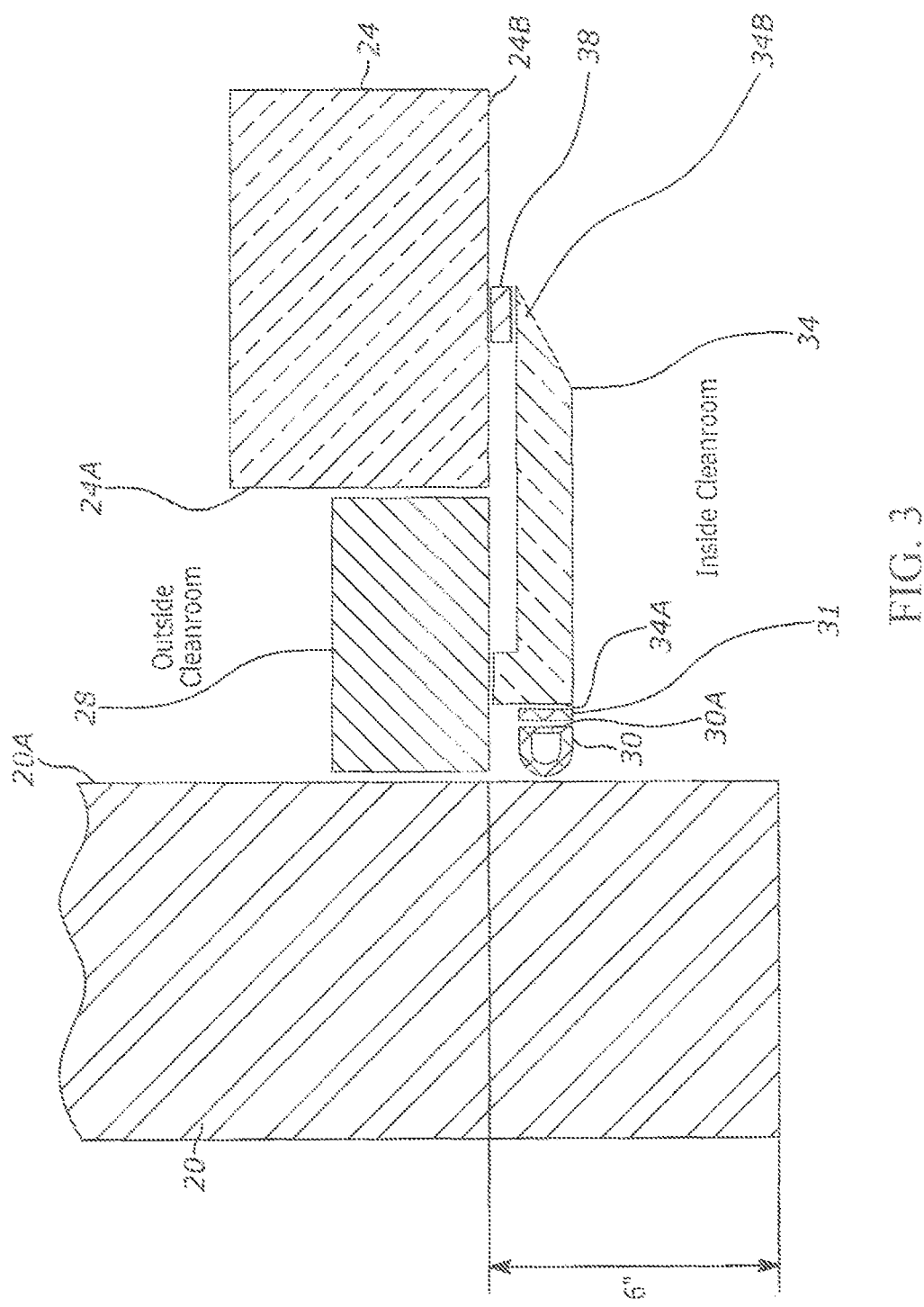
FIG. 3 is a sectional view looking down at a location along a vertical surface of an incubator, illustrating components for sealing gaps between the right vertical surface of the incubator and a cleanroom wall through which the incubator extends.

FIG. 3 is a sectional view taken at a location along a right-side vertical surface of an incubator 20 (that is, the right side when viewed from the incubator door (front surface) or from inside the cleanroom), illustrating the components that seal gaps between the incubator's right-side vertical surface and the cleanroom wall 24 through which the incubator extends. Note the identification in FIG. 3 of the regions inside and outside the cleanroom. The sealing components form a double vapor barrier between the space inside the cleanroom and the space outside the cleanroom. Generally, when used herein and as known by those skilled in the art, the term 'sealing' refers to a joint between two elements that has been sufficiently closed, by a third element, to prevent passage of contaminant particles through the sealed joint. Alternatively, the third element is referred to as "covering" the joint between the two elements.

One element of that double vapor barrier comprises a gasket 28 disposed between the right-side incubator wall surface 20A and a cleanroom wall surface 24A.

In one embodiment the gasket 28 has the following characteristics:

A density of between about 4 and 8 lb/ft^3

A 25% compression ratio with a deflection pressure of 1.0 psi (maximum)

Durometer (Shore 00): 5 (+/−5) (i.e., <10)

Material is semi-closed EPDM (ethylene propylene diene monomer) foam.

In one embodiment the gasket comprises Ensolite EFO form supplied by Armacell of Chapel Hill, NC.

As can also be seen in FIG. 3, the barrier further comprises:

a bulb-shaped gasket 30;

a frame 34; and a two-sided gasket tape 38

Generally, when referring to these elements, an incubator (or chamber) side of the element refers to a surface of the element (the gasket, or the frame, for example) that is proximate a surface of the incubator (chamber), where that surface can be either the right side surface of the incubator (chamber) or the left side surface of the incubator (chamber). Similarly, a 'wall-end' or 'wall-facing surface' refers to a surface of the gasket or frame that is proximate a wall surface (through which the incubator protrudes).

The gasket 28 is compressed (about a 25% compression ratio) between the surface 20A of the incubator 20 and the side surface 24A of the cleanroom wall 24. The resulting expansion forces retain the gasket in the FIG. 3 configuration. The compression ratio is essentially determined by the width of the cut-out relative to the width of the incubator 20.

The bulb-shaped gasket 30 is retained in the location of FIG. 3 by an adhesive 31 on a surface 30A (referred to as a flat surface) also affixed to a surface 34A of the frame 34. In one embodiment a material of the bulb gasket is similar to the material of the gasket 28, that is, EPDM with fully-closed cell. Other gasket shapes can be used in lieu of the bulb shape (e.g., a square or circular cross-section), but the illustrated bulb shape is preferred as it requires less compressive force/pressure to provide a secure seal and maintain that seal over time.

In one embodiment two-sided gasket tape 38 is disposed between a surface 24B of the wall 24 and an end 34B of the frame 34. The tape secures both the frame 34 and the bulb gasket 30 in position as shown in FIG. 3 and provides an effective seal.

A material of the frame 34 is typically a semi-rigid PVC composite that is resistant to harsh chemicals. Other materials with similar properties can also be used for the frame. Note from the various figures that an inclined surface defines one end of the frame. Generally, a simple frame composed of a semi-rigid material without gasket surfaces would not provide a sufficient seal. Thus, the present invention uses the gasket 28 and the bulb gasket 30 in conjunction with the frame for providing an effective seal.

As described above, the surface 20A in FIG. 3 is the right-side surface of the incubator when viewed from the incubator front surface, i.e., from inside the cleanroom. Thus FIG. 3 illustrates the components that form the secure seal between the wall of the cleanroom and the incubator right side surface. Similar components form a secure seal along the left-side surface of the incubator, i.e., between the left-side surface of the incubator and the adjacent cleanroom wall surface.

The components illustrated in FIG. 3 (and those disposed on the left-side surface of the incubator) extend vertically from a top incubator surface to a bottom incubator surface. Details of the mating of these vertical components and a bottom incubator skirt is discussed in conjunction with FIGS. 4, 5, and 6; a top incubator frame for sealing the top surface of the incubator and the adjacent wall surface is discussed in conjunction with FIG. 7.

Although tape and adhesive have been disclosed as securing the components of FIG. 3 in position and creating the seal, those skilled in the art are aware of other components that can be successfully used in lieu thereof. Additionally, as can be discerned from the foregoing description, tools are not required to assemble the components depicted in FIG. 3.

In one embodiment the incubator extends about six inches into the clean room, as indicated by dimension notation in FIG. 3. However, this distance is merely exemplary as certain installations may opt for larger or smaller distances. The key to placement of the incubator relative to the wall surface is to permit service on the incubator from outside the cleanroom. As discussed above, this feature significantly simplifies the servicing of the incubator.

Figure 4:
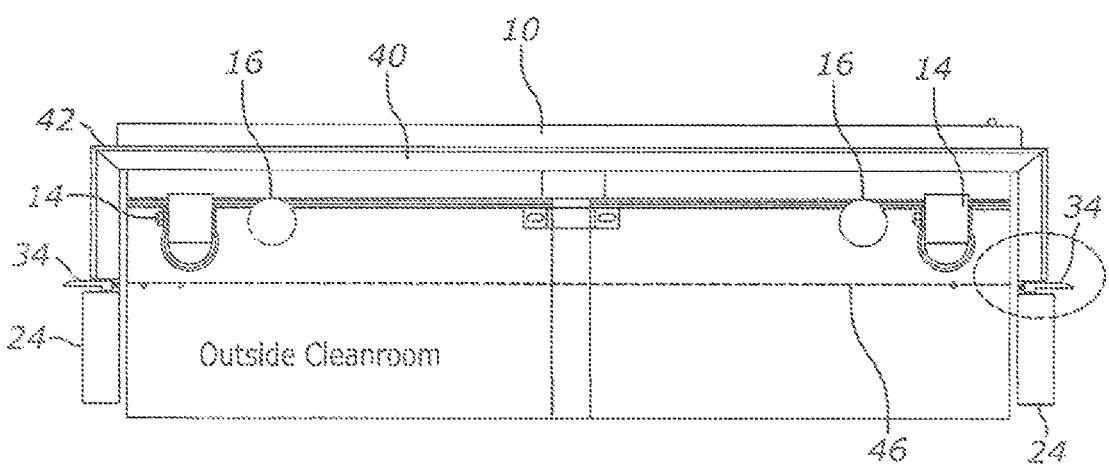
FIG. 4 illustrates components for sealing a bottom surface of an incubator and bottom-mounted chamber elements that must be accommodated to seal the bottom surface.
Figure 5:
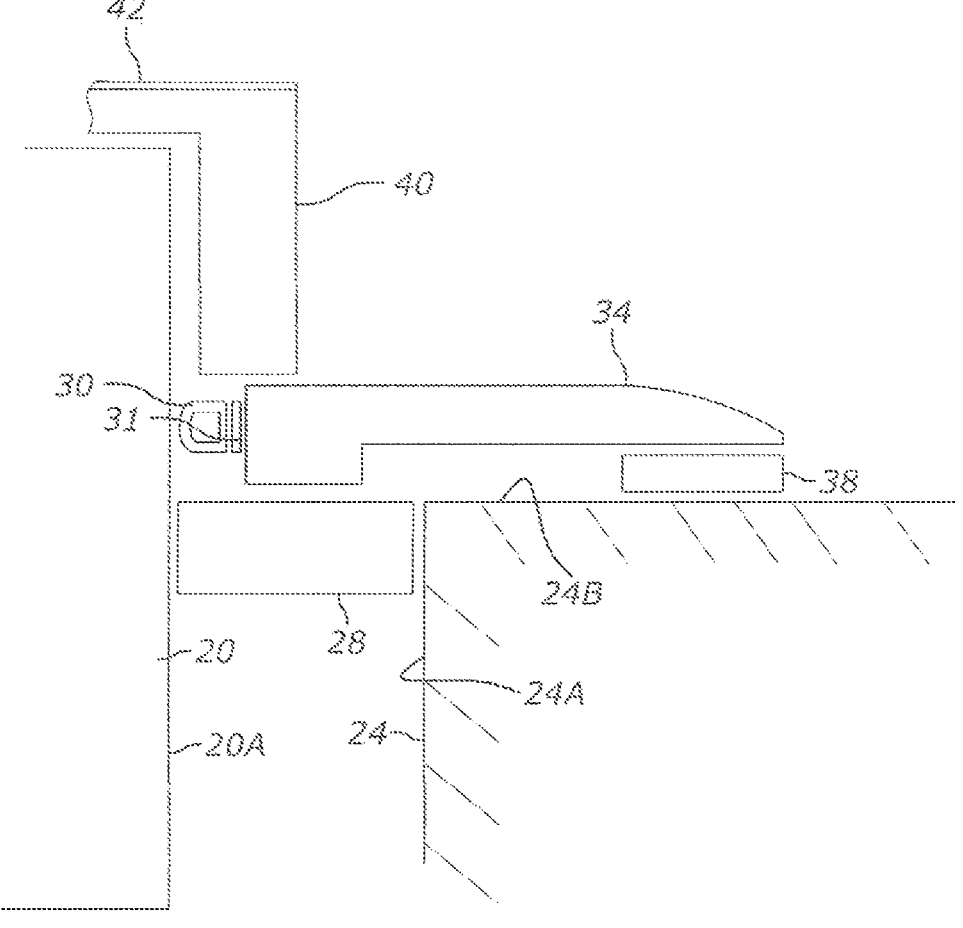
FIG. 5 is a close-up view of certain sealing components from FIG. 4.

A bottom view of an incubator and common incubator components is illustrated in FIG. 4 and a close-up view thereof in FIG. 5. A conventional incubator includes the caster wheels 14 and the leveling feet 16 illustrated in FIG. 4.

A phantom line 46 in FIG. 4 indicates the approximate location of the wall surface or plane of the wall when the incubator is disposed within a cleanroom wall opening.

FIG. 4 depicts a skirt 40 of the present invention that encloses the bottom surface of the incubator to maintain a seal along that surface. The skirt 40 is one of the components included in a kit of the present invention.

FIG. 4 and the close-up view of FIG. 5 depict the bottom surface components along the right side-surface of the incubator, as seen when looking up from the floor. FIG. 5 depicts the same components as shown in FIG. 3, but in FIG. 5 they are viewed from below whereas in FIG. 3 they are viewed from above. Recall that these components extend between the bottom surface and the top surface of the incubator. Thus, the detailed view of FIG. 5 illustrates the bottom surfaces of the gasket 28, the bulb gasket 30, the adhesive 31, the frame 34, and the adhesive gasket tape 38 where these components intersect the bottom skirt 40. At floor level, the bulb gasket 30 provides a barrier between the bottom surface of the incubator and the skirt.

The skirt 40 is secured by compressive frictional forces exerted on the skirt by a bulb gasket 50 (see FIG. 6) from above and by the weight of the incubator above the bulb gasket, and the floor below and by a bead of caulking 42 (see FIGS. 4 and 5) placed between the floor and a bottom surface of the skirt. Additionally, the bulb gasket 30 of FIG. 5 (this is the lower edge of the bulb gasket) is also in compression between the incubator side surface 20A (see FIG. 5) and the skirt.

Because the floor may not be entirely flat, the bead of caulking 42 provides an effective seal between the lower surface of the skirt 40 and the floor on which the incubator rests.

The skirt 40 is easily removable to allow easy access to the leveling feet 16 for leveling the incubator.

Figure 6:
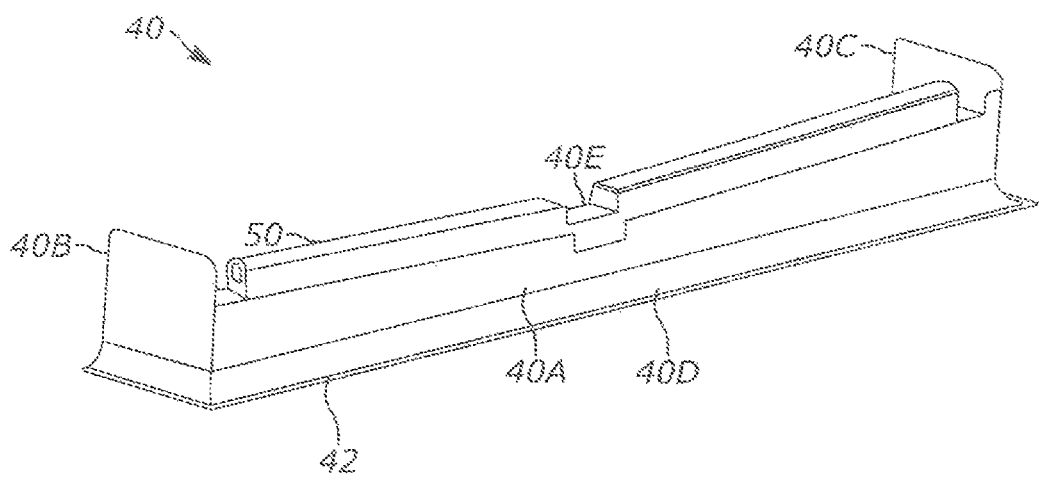
FIG. 6 illustrates the skirt shown in FIGS. 4 and 5.

FIG. 6 illustrates the skirt 40 comprising three surfaces 40A, 40B, and 40C to enclose the bottom region of the incubator, including the front surface of the incubator that extends into the cleanroom and a forward segment of each of the side surfaces that extend into the cleanroom. An upper region/edge of the side surfaces 40A and 40C is in contact with (forming a butt joint) respective side surfaces of the incubator. The caulk bead 42 extends along a bottom surface 40D to close a gap between the bottom surface 40D and the floor on which the incubator rests.

Note the coved shape 40D formed in the three surfaces 40A, 40B, and 40C. Note in particular the coved corners that provide easy cleaning of the skirt 40, unlike a corner or crack that can harbor contaminates and is difficult to clean.

A notch 40E is formed in the skirt through which tubes (e.g., metal tubing for condensate drips) and wires can pass from the incubator into the cleanroom.

Another bulb gasket 50 is disposed along the top surface 40F of the skirt 40, including within the notch 40E. Like the bulb gasket 30 on the left and right-side surfaces of the incubator, the bulb gasket 50 is maintained in a compressed between the skirt 40 and the bottom surface of the incubator to seal that gap.

Figure 7:
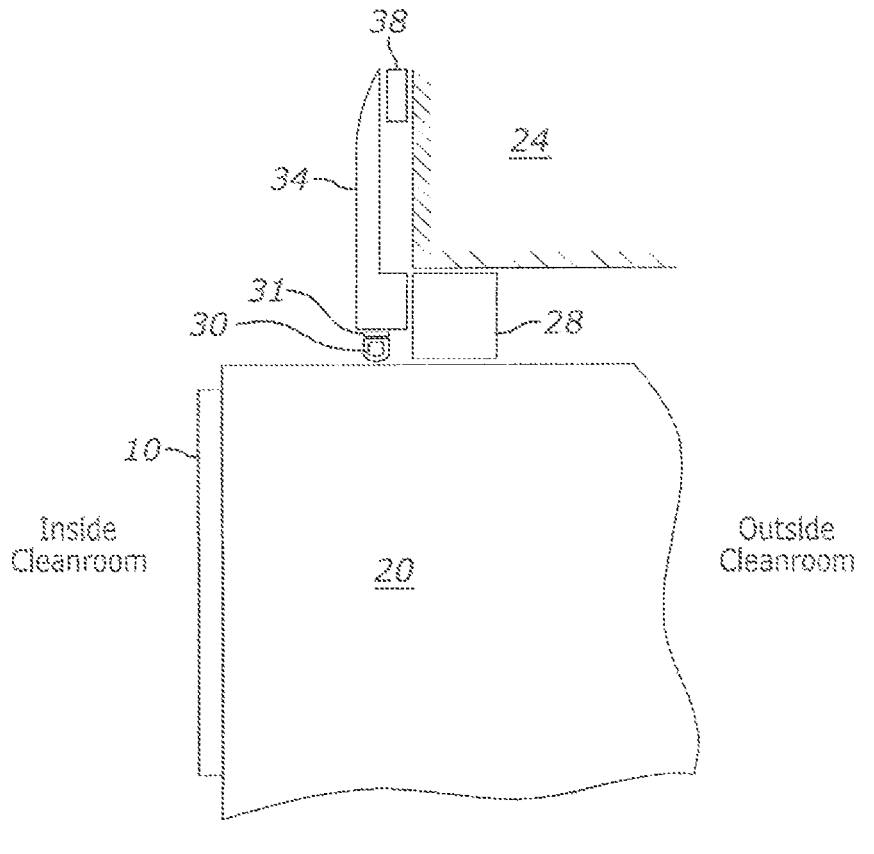
FIG. 7 illustrates components for sealing a top surface of an incubator.

A top surface 20B of the incubator 20 is illustrated in FIG. 7 with the various components that seal a gap between the top surface 20B and the wall 24. The components bearing the same reference numeral as in other figures perform the same function in FIG. 7, including the gasket 28, the bulb gasket 30, the adhesive 31, the frame 34, and the gasket tape 38. An incubator door 54 is also shown.

Mitered corners are formed at the junction between the horizontal frame along the top surface of the incubator and the two vertical frames extending along the right and left side surfaces of the incubator. This feature allows easy cleaning of the frames and prevents the accumulation of contaminants at those junctures.

The phrases "in contact with," "near contact with," and "substantially in contact with" have the meaning as known by those skilled in the art. In the present invention, generally, the contact must be sufficient to prevent the flow of contaminants through the joint defined by the elements "in contact."

The various gaskets and frames described herein are sized to accommodate specific distances based on the size of the wall opening through which the incubator protrudes. Also, although the frame and gasket members have been illustrated as defining an illustrated shape, those skilled in the art are aware that other shapes, depending on the installation, may be used with the same sealing effect.

Although described in the context of an incubator, the teachings of the present invention also apply to controlled-environmental chambers, refrigerators, freezers, and other laboratory equipment with a front door or panel for accessing interior components.

What is claimed is:

1. A kit of parts for use with an enclosure having access to an interior space through a door, the enclosure extending through a wall separating first and second spaces, a forward enclosure portion, including the door, protruding into the first space and a rearward enclosure portion protruding into second space, the parts of the kit for sealing gaps between enclosure right-side and left-side surfaces and proximate wall surfaces, and between a chamber top surface and a proximate wall surface, the kit of parts comprising:

a left-side vertically-oriented gasket for placing between the chamber left-side surface and a proximate wall surface, the left-side gasket extending from a chamber top surface to a chamber bottom surface;

a right-side vertically-oriented gasket for placing between the chamber right-side surface and an opposing wall surface, the right-side gasket extending from a chamber top surface to a chamber bottom surface;

a top horizontally-oriented gasket for placing between the chamber top surface and an opposing wall surface, the top gasket extending from the chamber left-side surface to the chamber right-side surface;

first and second left-side vertically-oriented material strips each extending from the chamber top surface to the chamber bottom surface and within the first space, the first material strip for sealing an interface between a surface of the left-side gasket and the chamber left-side surface and the second material strip for sealing an interface between another surface of the left-side gasket and a proximate wall service;

first and second right-side vertically-oriented material strips each extending from the chamber top surface to the chamber bottom surface and within the first space, the first right-side material strip for sealing an interface between a surface of the right-side gasket and the chamber right-side surface and the second right-side material strip for sealing an interface between another surface of the right-side gasket and a proximate wall surface;

first and second top horizontally-oriented material strip each extending from the chamber left-side surface to the chamber right-side surface and within the first space, the first top material strip for sealing an interface between a surface of the top gasket and the chamber top surface and the second top material strip for sealing an interface between another surface of the top gasket and an proximate wall surface;

a skirt for enclosing a bottom region of the chamber and disposed within the first space, the skirt comprising a front member and affixed thereto left-side and right-side skirt members, the left-side skirt member for installing in a spaced-apart relation from the chamber left-side surface and in contact with a lower end of the second left-side material strip, the right-side skirt member for installing in a spaced-apart relation from the chamber right-side surface and in contact with a lower end of the second right-side material strip; and a bottom horizontally-oriented material strip disposed between a top surface of the front member and a bottom surface of the chamber.

2. The kit of parts of claim 1, wherein the enclosure with access to an interior space via a door further comprises a controlled-environment chamber.

3. The kit of parts of claim 2, wherein the controlled-environment chamber further comprises an incubator, a refrigerator, or a freezer.

4. The kit of parts of claim 1, wherein the first space comprises a closed cleanroom and the second space comprises a space outside the cleanroom.

5. The kit of parts of claim 1, wherein the first left-side material strip, the first right-side material strip, and the bottom material strip each comprise a bulb gasket.

6. The kit of parts of claim 1, further comprising a caulking bead disposed between a bottom surface of the skirt and a floor surface on which the enclosure sets.

7. The kit of parts of claim 1, wherein a lower region of the front skirt member and a lower region of each of the left-side and right-side skirt members is coved shape.

8. The kit of parts of claim 1, wherein a material of each left-side and right-side gasket comprises a semi-closed EPDM (ethylene propylene diene monomer) with a density of between about 4 and 8 lb/ft^3.

9. The kit of parts of claim 1, wherein the left-side and right-side gaskets have a rectangular cross-sectional shape.

10. The kit of parts of claim 1, wherein the first left-side material strip comprises a left-side bulb gasket, the first right-side material strip comprises a right-side bulb gasket, the second left-side material strip comprises a left-side frame member, and the second right-side material strip comprises a right-side frame member.

11. The kit of parts of claim 10, wherein the left-side bulb gasket is disposed between a chamber-side end of the left-side frame member and the chamber left-side surface, and the right-side bulb gasket is disposed between a chamber-side end of the right-side frame member and the chamber right-side surface.

12. The kit of parts of claim 11, wherein each of the left-side and right-side bulb gaskets comprises a curved surface and an opposing flat surface, and wherein the curved surface of each of the left-side and right-side bulb gaskets for installing in contact with the respective chamber left-side surface and chamber right-side surface, and wherein the opposing flat surface of each of the left-side and right-side bulb gaskets for installing in a contact with the chamber-side end of the respective left-side and right-side frame members.

13. The kit of parts of claim 12, wherein the flat surface of the left-side bulb gasket is joined to the chamber-side end of the left-side frame member by a first adhesive and the flat surface of the right-side bulb gasket is joined to the chamber-side end of the right-side frame member by a second adhesive.

14. The kit of parts of claim 10, wherein a material of the left-side bulb gasket and the right-side bulb gasket comprises fully-closed cells of EPDM.

15. The kit of parts of claim 10 wherein a wall-end of the left-side frame member is affixed to a proximate wall surface and a wall-end of the right-side frame member is affixed to a proximate wall surface.

16. The kit of parts of claim 15, wherein a first adhesive is disposed between a wall-facing surface of the left-side frame member and a proximate wall surface and a second adhesive is disposed between a wall-facing surface of the right-side frame member and a proximate wall surface.

17. The kit of parts of claim 16, wherein the first and second adhesives each comprise an adhesive tape gasket.

18. The kit of parts of claim 1, wherein a material of the left-side and right-side gaskets is in compression when disposed between the respective chamber left-side and right-side surfaces and an opposing wall surface.

19. The kit of parts of claim 1, wherein the left-side and right-side gaskets, the first and second left-side material strips, and the first and second right-side material strips form a double vapor barrier between the first space and the second space.

* * * * *